United States Patent [19]

Leonard et al.

[11] Patent Number: 4,581,022

[45] Date of Patent: Apr. 8, 1986

[54] DENTAL SYRINGE

[75] Inventors: Henri Leonard, Besancon; Michel Seigneurin, St-Cergues - Douvaine, both of France

[73] Assignee: MICRO-MEGA S.A., Besancon, France

[21] Appl. No.: 547,768

[22] Filed: Nov. 1, 1983

[30] Foreign Application Priority Data

Nov. 3, 1982 [FR] France .............................. 82 18546
Aug. 3, 1983 [FR] France .............................. 83 12932

[51] Int. Cl.$^4$ ............................................ A61M 5/315
[52] U.S. Cl. ..................................... 604/224; 222/391
[58] Field of Search ............ 604/224, 227, 207, 208, 604/209, 210; 433/89, 90, 80, 83; 222/391, 340

[56] References Cited

U.S. PATENT DOCUMENTS

| 201,443 | 3/1878 | Parker | 604/209 |
|---|---|---|---|
| 2,266,998 | 12/1941 | Smith | 604/209 X |
| 2,472,116 | 6/1949 | Maynes | 604/224 X |
| 2,585,815 | 2/1952 | McLintock | 604/209 |
| 3,051,172 | 8/1962 | Bruchhaus | 604/224 X |
| 3,977,574 | 8/1976 | Thomas | 604/209 X |
| 4,444,560 | 4/1984 | Jacklick | 604/224 |

Primary Examiner—Stephen C. Pellegrino
Attorney, Agent, or Firm—Robert E. Burns; Emmanuel J. Lobato; Bruce L. Adams

[57] ABSTRACT

A precision injection system for intralignmental anesthesia and the like having a syringe with a tubular handle portion which is removably connected a tubular headpiece as a longitudinal extension thereof. The headpiece receives a carpule cartridge with injection contents monitored during injections through elongate windows on opposite sides of the headpiece. A dosing plunger housed in the handle portion in a retracted start position is activated by a servo-dosing lever and advances incrementally axially into the headpiece for delivery of metered quantities of the contents of the carpule cartridge each time the servo-dosing lever is actuated. Provision is made for semiautomatic resetting of the dosing plunger to a retracted start position by depressing a resetting key and raising the syringe to a generally vertically raised position. The dosing plunger has a rack thereon activated by a ratchet cooperative with the servo-dosing lever so that a reduction in the normal pressure applied to the servo-dosing lever is effected in making the injections.

11 Claims, 7 Drawing Figures

DENTAL SYRINGE

The present invention relates to a dental syringe for inter-ligamentous injections, of the type generally comprising an injection needle, a container containing the product for injection and a piston controlling the displacement of the bottom of the container.

Syringes of this type have already been described, for example in FR Pat. No. 1,583,163 in the name of the above Applicant Company.

However, syringes of this kind are not suitable as such for the injection of products into the ligaments situated between the bone of the jaw and the tooth.

The space between the bone and the tooth is in fact narrow and requires the introduction of a very fine and flexible needle. A very high injection pressure must therefore be applied to the product to enable it to pass through this needle and to be expelled.

Pressure applied to the piston merely with the palm of the hand, as is the case with conventional syringes, is not appropriate.

The subject of the invention is consequently a precision injection system having a syringe for inter-ligamentous injections which makes it possible to remedy these disadvantages. According to the invention this result is obtained with a dental syringe for inter-ligamentous injections, of the type comprising an injection needle, a container or carpule containing the product for injection and a dosing piston controlling the displacement of the bottom of the container, characterised in that the displacement of the dosing piston towards the container is controlled by a servo dosing lever comprising a ratchet co-operating with a rack arranged on the dosing piston, providing a reduction in the manual pressure applied to the servo-dosing lever by the user.

Since the force of the manual pressure applied by the user is multiplied, the explusion of the product or content from the container can take place without problems.

Furthermore, since the force applied by the user is nevertheless smaller than with the syringes of prior art, this results in better working conditions and a greater accuracy in the operation.

According to a first embodiment of the invention, the product for injection is a liquid which is contained in a "carpule" such as described in the above-mentioned earlier patent, that is to say in the form of a small oblong container whose rear end consists of a movable disc, and whose front end is closed by a rubber plug which is intended to be pierced by the injection needle.

In this embodiment, the invention also provides for the addition, between the front end of the carpule holder and the carpule, of a sleeve-shaped component protecting the stopper of the carpule against accidental tears which could result from the deformation of the stopper under the pressure of the liquid contained in the carpule. According to the invention this sleeve surrounds the rear part of the needle and opens out at its rear end to match the shape of the carpule holder, the middle portion of this end having a raised part which slightly presses the rubber stopper of the carpule in the region of the end of the needle.

According to a second embodiment, the product for injection is a paste and, in this case, in place of the carpule just described, the invention provides for a paste container terminating at the front by an injection nozzle, which may be angular, and at the rear by an elastic plug subject to the action of an auxiliary piston which can move in a component serving as a container holder and being itself subject to the action of the main piston contained in the body of the syringe and activated by the means described above. A return spring tends to separate this auxiliary piston from this plug, the stroke of this auxiliary piston being limited by two end-stops which are lodged in the container holder.

In the first embodiment, the carpule is introduced through a rear opening of the container holder or viewing chamber of a headpiece. In the second, with the auxiliary piston preventing this rear entry of the container, the container is introduced through an opening provided in the front part of the container holder.

The invention will be understood better with the help of the following description, made with reference to the attached drawings in which.

Figure 1:
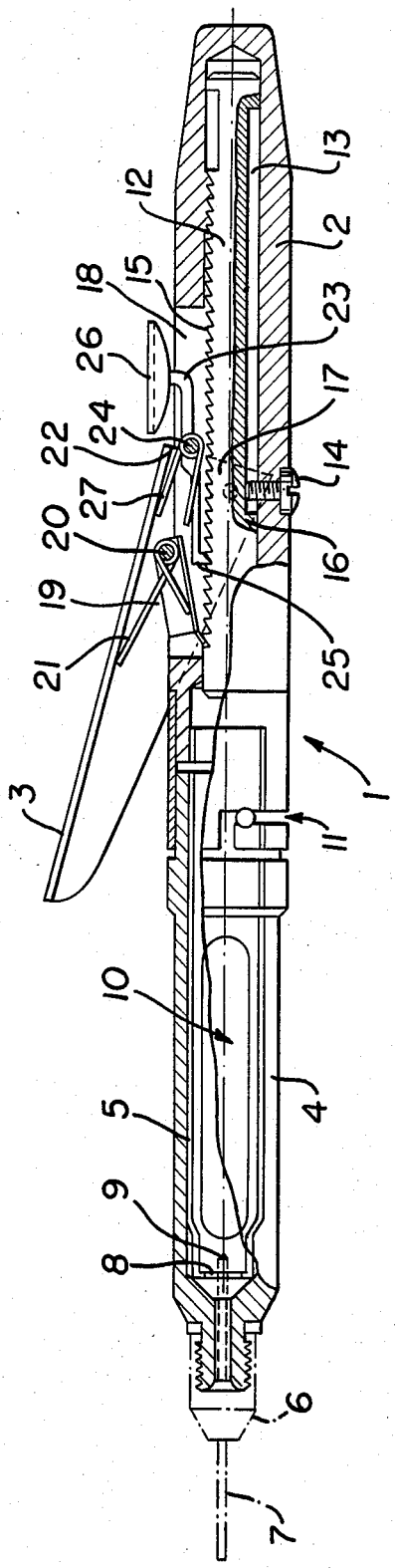
FIG. 1 is a view, in partial longitudinal cross-section, of a syringe according to the first embodiment of the invention.
Figure 3:
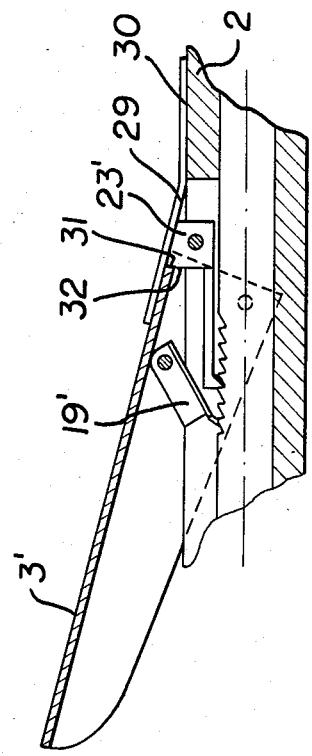
FIG. 3 is an alternative way of making the reduction device of the syringe of FIG. 1, in longitudinal cross-section and in part-view.
Figure 2:
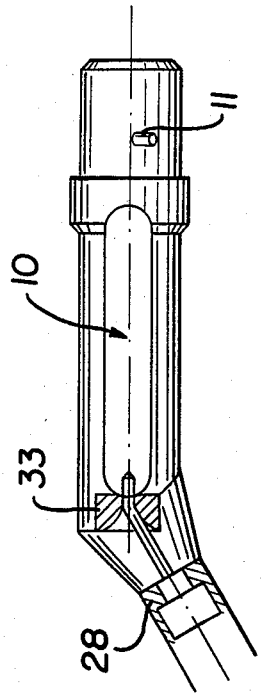
FIG. 2 is an alternative form of FIG. 1 with an inclined needle support.

Reference will first be made to FIGS. 1 to 3, that is to say to the embodiment of the invention in which the syringe is intended for the inter-ligamentous injection of liquid products.

In this case the syringe (1), as shown in its entirety in FIG. 1, comprises essentially:

a body or handle portion (2) to which is articulated a servo dosing lever (3) for controlling the syringe, a carpule support (4) or tubular headpiece having a viewing chamber into which the carpule (5) has been loaded, an end component (6) comprising an injection needle (7).

The carpule (5) is, in a known manner, in the form of an oblong container enclosing the liquid for injection. It comprises, at one of its ends, a rubber plug (8) which will be pierced by the rear portion (9) of the needle (7). For this reason, it may be possible to use only part of the carpule. The bottom of the carpule consists of a disc which can move in translation and which, by its movement, pushes the liquid for injection towards the needle.

The carpule support (4) comprises an opening (10) on each side as axial or elongated windows permitting the level of the carpule contents to be observed for carpule control.

To permit the insertion and the withdrawal of the carpules, the carpule support (4) is connected to the body (2) so that it can be detached, for example by a bayonet system or catch (11) of a conventional construction which will therefore not be described in further detail.

A cylindrical piston or dosing plunger (12), sliding in the body (2), comprises a longitudinal guiding groove (13) which co-operates with a key (14) fixed integrally to the body (2). In this way, the piston cannot rotate around its longitudinal axis.

A rack (15), whose teeth are directed towards the rear of the syringe, is cut on a portion of the piston (12) parallel to a generatrix.

A control lever (3), preferably of a U-shaped cross-section, is articulated, as indicated earlier, to the body (2), the lever being thus capable of being raised in rotation around two half-axles (16) fixed in line with each other on either side of the body (2). The lever (3) thus straddles the body (2) with its articulation flanges (17).

An opening (18) in the body (2) is provided between the lever (3) and the body in the region where the said body is covered by the lever.

On the lever (3) there is mounted a ratchet (19) pivoting around an axle (20) which is fixed to the said lever. A spring (21) presses, on the one hand, on the ratchet (19) and, on the other hand, on the interior of the lever (3), tending to separate it from the body (2) on which it abuts onto a shoulder (22).

Furthermore, a detent lever (23) is mounted pivoting on an axle (24) fixed in the handle portion. With its catch end (25), the detent lever (23) engages with the rack (15) and at its other end it comprises, projecting outside the body (2), a button or resetting key (26) to which the user can apply manual pressure. A spring (27) tends to bring the catch end (25) of the lever into engagement with the rack (15), the other end of the spring being supported by the inner face of the servo-dosing lever (3).

If the button or resetting by (26) is pressed, the catch end (25) of the detent lever (23) disengages from the rack and its movement is transmitted to the ratchet (19) which is thus also disengaged from the rack.

The operation of this syringe is as follows. To start with, the piston is placed in the position shown in FIG. 1. For this purpose, the syringe is held vertically, the needle upwards, and the button or resetting by (26) is pressed. The dosing plunger, disengaged from the ratchet (19) and from the catch end (25) of the detent lever, descends to the bottom of the body or handle portion (2) under the effect of its weight alone.

The carpule is then introduced into its support and the latter is coupled to the body by means of the bayonet system (11). The whole is then ready for use.

For this purpose, by pressing on the lever (3), in fact by a simple repeated pressure with the thumb, as if pumping, the axle (20) moves relative to the axles (16). The ratchet (19) then pushes, by one tooth, the rack (15) and hence the piston (12) which in its turn pushes the rubber disc forming the bottom of the carpule. The force of the finger pressing on the lever is thus transmitted to the disc and thus to the contents of the carpule with a multiplication coefficient, for example of the order of five.

As soon as the user releases the pressure on the lever (3), the latter returns into the raised position under the effect of the spring (21). During this operation, the detent lever (23) keeps the piston in position with its catch end (25). The operation can then be repeated, with the piston moving forward by a distance corresponding to the pitch of the rack, or to a multiple of the pitch at each pressure on the lever (3).

In the embodiment of FIG. 1, the needle (7) is mounted on the support or nozzle (6). The nozzle (6) can be threaded and fixed integrally to the headpiece (4) or can be mounted on it in a detachable manner, for example by means of a bayonet system.

In the alternative version of FIG. 2, it is preferable that the needle support should be mounted in a detachable manner.

In this embodiment the needle is inclined relative to the axis of the syringe, which is more convenient for certain injections.

In this case the operation is as follows:
placing the needle on the carpule support,
introduction of the carpule into its support,
coupling the carpule support to the syringe body,
injection.

In this case, to ensure that the needle penetrates correctly with its rear part into the carpule, a barrel (33) having a conical passage can be provided in the support, the end of the needle sliding into the cone in such a way that its rear end (9) is always substantially parallel to the longitudinal axis of the carpule.

In the alternative embodiment of FIG. 3, a flexible tongue (29), which is fixed at (30) on the body (2), presses, on the one hand, the back of the lever (23'), identical in function to the lever (23), and, on the other hand, the back of the lever (3'), identical in function to the lever (3), keeping them, as well as the ratchet, in position.

When the user presses the lever (3') the piston moves forward by the same mechanism as that described above. As soon as pressure is released, the spring (29) returns the lever (3') into the raised position.

To disengage the ratchet (19') and the lever (23') from the piston rack it suffices to pull the lever (3') beyond its equilibrium position determined by the rest position of the tongue (29). The face (31) of the lever then pushes the face (32) of the lever (23') and tips it up, releasing it from the rack.

Figure 4:
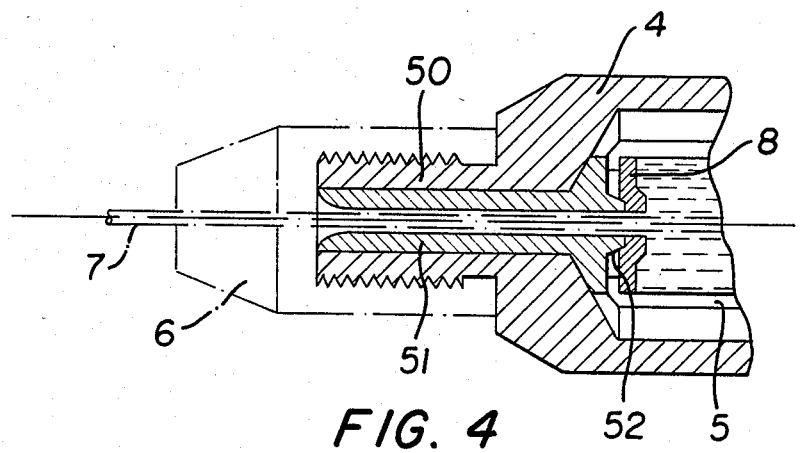
FIG. 4 shows the sleeve for protecting the carpule, with the needle in place.
Figure 5:
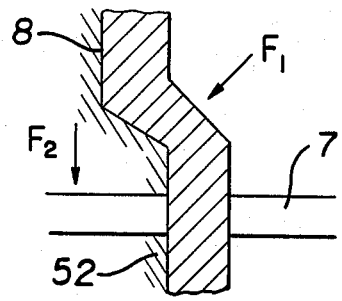
FIG. 5 is a large-scale diagram showing the shape of the carpule stopper.

Reference is now made to FIGS. 4 and 5, it is seen that in the front part (50) of the carpule holder (4) there is provided a sleeve (51) which surrounds the needle (7) from the bottom of the end component (6) as far as the rubber plug (8) of the carpule (5). As can be seen, the rear of the sleeve (51) is of a flared shape so that it is supported on the forward face of the carpule holder (4), while having an appendix (52) which presses the plug (8) around the needle (7).

The first purpose of this appendix (52) is to prevent this plug from bulging under the influence of the pressure of the liquid, thereby risking the occurrence of a tear in the plug when it is pierced by the needle, particularly with the angled version (FIG. 2).

Moreover, when the pressure of the liquid contained in the carpule increases at the instant of use, the resultant of the pressure forces acting on the plug (8) is resolved, as shown in FIG. 5, into force $F_1$ acting obliquely and a force $F_2$ acting towards the axis, that is to say towards the needle. In other words, at the instant of use the plug (8) presses very hard on the needle, helping thereby to prevent leaks.

Figure 6:
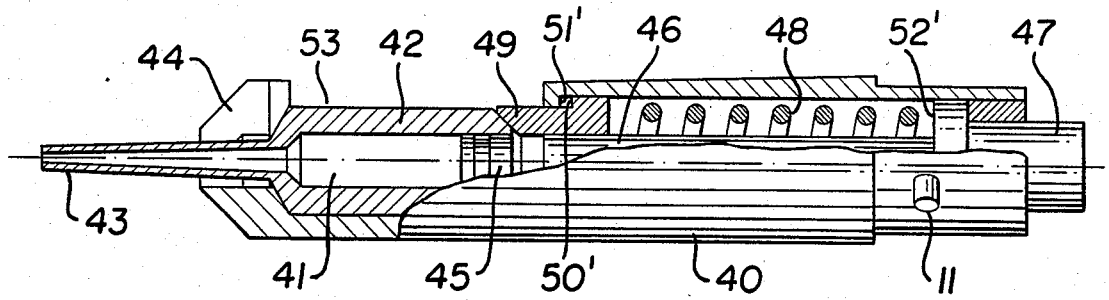
FIG. 6 is a side view, with partial cut-away, of the container holder intended for the embodiment of the invention intended for the injection of pasty products.
Figure 7:
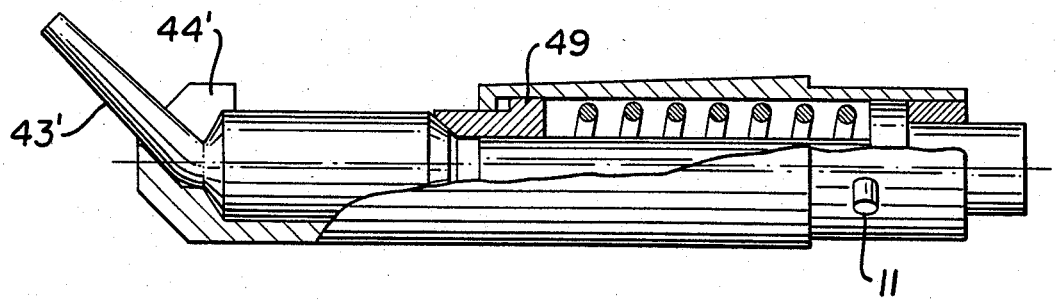
FIG. 7 is a view similar to FIG. 6, in the case where the injection nozzle is angled.

Reference will not be made to the alternative version illustrated in FIGS. 6 and 7, which represents the embodiment of the invention in which the product for injection is pasty.

In these figures, (40) shows the container holder which is analogous to the carpule holder (4) of the preceding embodiment, except insofar as its front part is concerned. This container holder is of overall cylindrical shape and forms a housing in which are placed:

a container intended to contain a pasty product, designated by the general reference (41) and comprising a main cylindrical, relatively thick-walled body (42) and a tapered nozzle (43) protruding from the forward end (44) of the container holder; this container is closed at its rear end by an elastic plug (45);

an auxiliary piston (46) having the same diameter as the plug (45) and a rear part (47) which projects outside the container holder so as to come into contact with the main piston (12) (not shown in these figures) as the instant when the said container carrier is coupled with the syringe body at (11). This auxiliary piston is pressed backwards by a spring (48) supported, at the front, by a ring (49) lodged in the container holder and immobilised against any axial forward displacement by means of a shoulder (50') co-operating with a corresponding rim (51') of the container holder and, at the rear, by a shoulder (52') of the auxiliary piston; when at rest, the piston is therefore in the position shown in the drawing.

The container (42), which cannot be introduced into the container holder from the rear because of the presence of the auxiliary piston (40), is introduced through an opening (53) arranged longitudinally in the container holder, from the front end (44) as far as the rim (51'). For this purpose, the ring (49) has a bevelled edge (54) whose function is both to facilitate this insertion and then to keep the container in place.

The operation of the device is identical to that of FIGS. 1 and 2. After coupling the container holder, fitted with a container, to the body of the syringe by applying manual pressure, the user produces a forward step-wise movement of the main piston (12) which transmits its displacement to the auxiliary piston (46) against the spring (48). The auxiliary piston comes into contact with the plug (45) and, continuing its one-directional movement, gradually pushes this plug inside the container (41). The plug in its turn then acts as a piston on the pasty product which is gradually propelled towards the nozzle (43) from which it is slowly expelled into its zone of use. For example, by a series of pressures on the lever (3) of the syringe, the user would be able, effortlessly, to propel a pasty amalgam into a dental cavity.

The alternative version of FIG. 7 shows a modification of the head (44') of the container holder, permitting the use of a nozzle (43') which is oblique relative to the general axis of the device.

We claim:

1. A precision injection system for intraligmental anesthesia and the like comprising, an intraligmental syringe having a tubular handle portion and at least one exchangeable tubular headpiece mountable on and dismountable from the handle portion for exchange thereof with other individual headpieces, means for removably and releasably mounting the headpiece coaxially with the tubular handle portion extending longitudinally therefrom for jointly defining therewith a tubular syringe, the headpiece having at an end thereof a threaded nozzle for removably mounting individual replaceable injection needles each having a needle point, the headpiece defining a viewing chamber for carpule control and dimensioned for receiving therein and containing a carpule cartridge with contents therein to be injected, a dosing plunger housed in the handle portion in a retracted starting position, a servo-dosing lever mounted externally on the tubular handle portion for activating the dosing plunger for incremental gradual advancing movement axially out of said handle portion from the starting position into said viewing chamber of the headpiece to effect delivery of metered quantities of contents of the carpule cartridge for flow through the needle point of an injection needle in dependence upon the incremental axial advancing movement of the dosing plunger, activating means on the tubular handle portion coactive with the servo-dosing lever and dosing plunger for activating the dosing plunger incrementally each time the servo-dosing lever is depressed, and means comprising a resetting key on the handle portion actuatable manually for semiautomatic retraction of the dosing plunger to the retracted starting position.

2. A precision injection system for intraligmental anesthesia and the like according to claim 1, in which the threaded nozzle is unitary with the headpiece and in communication with the interior thereof and the nozzle being angled relative to the headpiece longitudinal axis.

3. A precision injection system for intraligmental anesthesia and the like according to claim 1, in which said viewing chamber is elongated and has elongated windows axially thereon on opposite sides for viewing for carpule cartridge control.

4. A precision injection system for intraligmental anesthesia and the like according to claim 1, in which said means for removably and releasably mounting the handpiece coaxially with the tubular handle portion comprises a bayonet catch.

5. A precision injection system for intraligmental anesthesia and the like according to claim 1, including a plurality of individual headpieces exchangeable on the tubular handle portion with the first-mentioned headpiece, each headpiece having an elongated viewing chamber for carpule control and each chamber having elongated windows axially thereon on opposite sides for viewing for carpule cartridge control.

6. A precision injection system for intraligmental anesthesia and the like according to claim 1, in which said dosing plunger has an axial rack thereon, and in which said actuating means comprises a ratchet engaging the rack on said dosing plunger actuated by said servo-dosing lever for advancing the dosing plunger axially incrementally.

7. A syringe according to claim 6, in which the dosing plunger has a longitudinal guiding groove, a key fixed integrally to the handle portion extending into said groove to keep the dosing plunger from rotating about its longitudinal axis.

8. A syringe according to claim 6, including an axle on which said ratchet is mounted for pivoting thereon, said axle being fixed to the servo-dosing lever, tending to separate said servo-dosing lever from the handle portion on which it abuts onto a shoulder.

9. A syringe according to claim 6 including a detent lever mounted pivotally, a pivot axle for the detent lever fixed in the handle portion, said detent lever having a catch end and engaging through said catch end with the rack and having at its other end said resetting key, a spring tending to apply said catch end of the detent lever into engagement with the rack, the other end of the spring resting on the inner face of the servo-dosing lever.

10. A syringe according to claim 6, characterised in disengaged from the rack, the catch end of the lever drives the ratchet together with it.

11. A syringe according to claim 6, in which said nozzle is fixed to said headpiece, and in which an injection needle is mounted on said fixed nozzle.

* * * * *